United States Patent [19]
Gruber et al.

[11] 4,202,834
[45] May 13, 1980

[54] COPOLYMERIZABLE, ULTRAVIOLET LIGHT ABSORBER (2-CYANO-3,3-DIPHENYLACRYLOXY) ALKYLENE ETHYLENIC ETHERS

[75] Inventors: Bruce A. Gruber, Bloomingdale; Donald H. Lorenz, Basking Ridge, both of N.J.

[73] Assignee: GAF Corporation, New York, N.Y.

[21] Appl. No.: 22,370

[22] Filed: Mar. 20, 1979

[51] Int. Cl.$^2$ ............................................... C07C 21/70
[52] U.S. Cl. ........................ 260/465 D; 260/45.85 A
[58] Field of Search ................... 260/465 D, 45.85 A

[56] References Cited
U.S. PATENT DOCUMENTS 3,644,466   2/1972   Strobel et al. .................. 260/465 D

*Primary Examiner*—Dolph H. Torrence
*Attorney, Agent, or Firm*—Walter C. Kehm; Walter Katz

[57] ABSTRACT

This invention relates to copolymerizable ultraviolet light absorber compounds having the formula:

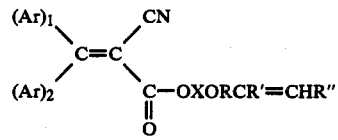

where $(Ar)_1$ and $(Ar)_2$ are aromatic carbocyclic nuclei of the benzene and naphthalene series and are independently selected from phenyl or phenyl substituted with alkyl, halo, alkoxy, carboxy, carbalkoxy, cyano, acetyl, benzoyl, phenyl, alkyl phenyl, phenoxy phenyl, alkyl substituted phenoxy, or alkoxy phenyl substituted phenyl, and naphthyl;

X is alkylene, $C_2$–$C_{17}$, unsubstituted, or halo, cyano, alkyl, alkoxy, alkoxyalkyl, or alkoxyalkyleneoxy, $C_1$–$C_6$ substituted.

R is alkylene, oxyalkylene, alkyleneoxyalkylene, or benzylene, $C_1$–$C_{10}$, unsubstituted or substituted with hydroxy, and R' and R" are independently hydrogen or alkyl, $C_1$–$C_6$.

10 Claims, No Drawings

COPOLYMERIZABLE, ULTRAVIOLET LIGHT ABSORBER (2-CYANO-3,3-DIPHENYLACRYLOXY) ALKYLENE ETHYLENIC ETHERS

BACKGROUND OF THE INVENTION

1. Field of the Invention

This invention relates to novel copolymerizable ultraviolet light absorber compounds, and, more particularly, to 2-cyano-3,3-diphenylacryloxy alkylene ethylenic ether compounds which are copolymerizable with vinyl monomers to provide polymer materials having improved resistance to degradation to light.

2. Description of the Prior Art

Various organic compounds exhibit the power to absorb electromagnetic radiation and can be incorporated in various plastic materials such as transparent sheets which act as filters for all the radiation passing through and will transmit only such radiations as are not absorbed by the sheet and/or the absorbing agent. Such filters find use in many technical and commercial applications.

Numerous cyano acrylic compounds have been suggested as absorbents for the range of radiations described above. For specific compounds, see U.S. Pat. Nos. 3,081,280; 3,272,810; 3,644,466; 3,256,312 and 3,215,724. These ultraviolet absorbers are mechanically mixed with the plastic materials to prevent discoloration and degradation of the material. However, it has been observed that such absorbers sometimes fail or are blocked out of the plastic under adverse weather conditions, before the lifetime of the protected material. Also, it is not possible to use all of these ultraviolet absorbers with radiation curing of the plastic material. Another disadvantage of these ultraviolet absorbers is the high amount of absorber needed for protection of some materials.

Accordingly, it is an object of the present invention to provide novel copolymerizable ultraviolet light absorber compounds which are substantially free of the disadvantages of the prior art.

A particular object of this invention is to provide novel compounds which can be copolymerized directly with the plastic material to provide more permanent ultraviolet light protection.

A specific object is to provide ultraviolet light absorber compounds containing a copolymerizable ethylenic group.

These and other objects and features of the invention will be made apparent from the following more particular description of the invention.

SUMMARY OF THE INVENTION

What is provided herein are improved, novel copolymerizable ultraviolet light absorber compounds of the formula:

$$(Ar)_1\!\!\diagdown_{\!\!\diagup}\!\!C\!=\!C\!\diagdown_{\!\!\diagup}\!\!\begin{array}{c}CN\\C\!-\!OXORCR'\!=\!CHR''\\\|\\O\end{array}$$
$$(Ar)_2$$

where $(Ar)_1$ and $(Ar)_2$ are aromatic carbocyclic nuclei of the benzene and naphthalene series and are independently selected from phenyl or phenyl substituted with alkyl, halo, alkoxy, carboxy, carbalkoxy, cyano, acetyl, benzoyl, phenyl, alkyl phenyl, phenoxy phenyl, alkyl substituted phenoxy, or alkoxy phenyl substituted phenyl, and naphthyl;

X is alkylene, $C_2$–$C_{17}$, unsubstituted or substituted with halo, cyano, alkyl, alkoxy, alkoxyalkyl, or alkoxyalkyleneoxy, $C_1$–$C_6$;

R is alkylene, oxyalkylene, alkyleneoxyalkylene, or benzylene, $C_1$–$C_{10}$, unsubstituted or substituted with hydroxy, and, R' and R" are independently hydrogen or alkyl, $C_1$–$C_6$.

In the best mode of the invention, $(Ar)_1$ and $(Ar)_2$ are phenyl, X is —$C_2H_4$—, R is alkylene, —$CH_2$—, and R' and R" are both hydrogen.

DETAILED DESCRIPTION OF THE INVENTION

Suitable $(Ar)_1$ and $(Ar)_2$ groups are given in U.S. Pat. No. 3,644,466, including representative starting benzophenone compounds. In the best mode of the invention, both $(Ar)_1$ and $(Ar)_2$ are phenyl.

The X groups are unsubstituted or substituted alkylene radicals, $C_2$–$C_{17}$. The preferred groups are unsubstituted lower alkylene, $C_2$–$C_6$, which are derived synthetically from ethylene glycol, propylene glycol, butanediol, and the like. The best mode is represented by —$CH_2$—$CH_2$—.

The —RCR'=CHR" radical is copolymerizable with vinyl monomers so that the ultraviolet absorber becomes an integral part of the polymer. Suitable radicals are allyl, crotyl, methylpropenyl, vinylbenzyl, vinyloxyethyl, allyloxy-2-hydroxypropyl, and 2-hydroxy-3-butenyl. The best mode is represented by allyl.

The compounds of the invention contain ultraviolet light absorber and copolymerizable portions in the same molecule. These portions are effectively separated by the X radical so that each can perform its own function without interference from the other. Therefore, the absorber portion does not inhibit the copolymerization, and the ethylenic radical does not affect the light absorbing properties of the molecule.

The novel compounds of the invention may be prepared by alkylation of 2-hydroxyalkyl 2-cyano-3,3-diphenyl acrylate with an ethylenic halide.

In this method, the hydroxy group of a hydroxyalkyl cyano acetate first is protected by acylation with a group convertible by hydrolysis to the hydroxy compound, e.g. with an acetyl group, to provide the corresponding acetoxyalkyl cyanoacetate. The protected compound then is condensed with a benzophenone in a Knoevenagel reaction to provide the acetoxyalkyl 2-cyano-3,3-diphenyl acrylate in good yield. Subsequent acid hydrolysis of the protecting acetyl group affords the corresponding hydroxy intermediate, which is then directly alkylated with a suitable ethylenic halide to give the desired compounds.

This method is summarized below:

METHOD $$\text{CH}_2\!\!\diagup_{\!\!\diagdown}\!\!\begin{array}{c}CN\\C\!-\!OH\\\|\\O\end{array} + \text{HOXOH} \xrightarrow{\text{esterification}} \text{CH}_2\!\!\diagup_{\!\!\diagdown}\!\!\begin{array}{c}CN\\C\!-\!OXOH\\\|\\O\end{array} \quad (a)$$

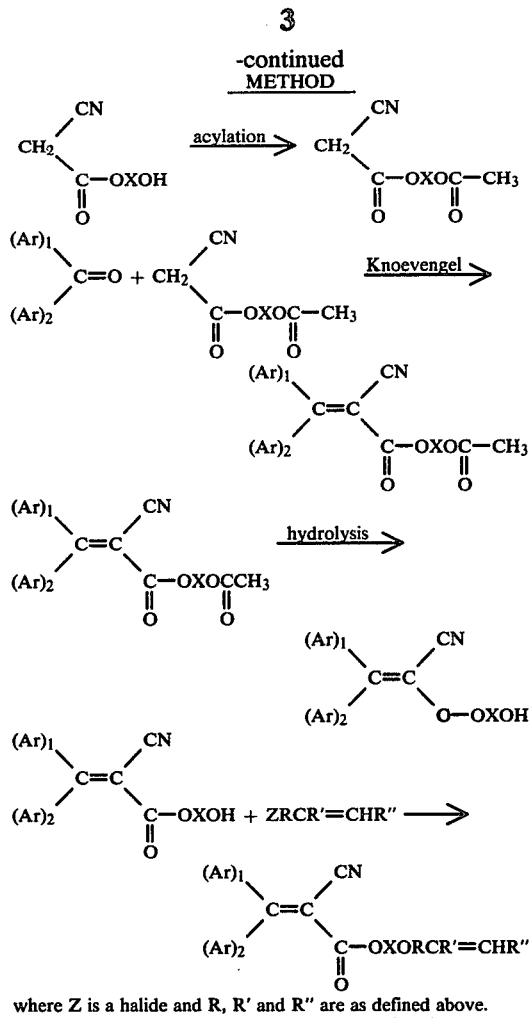

where Z is a halide and R, R' and R'' are as defined above.
Typical X groups are —CH₂CH₂—, —CH₂CH₂CH₂—
CH₂CH₂CH₂CH₂—, and the like.
Representative RCR'=CHR'' radicals are —CH₂—
CH=CH₂ (allyl), —CH=CHCH₃ (crotyl), —CH₂C=CH₂ (2-methyl-1-propenyl),
       |
       CH₃

—CH₂—⟨phenyl⟩—CH=CH₂ (vinylbenzyl),

—CH₂CH₂OCH=CH₂ (vinyloxyethyl),

—CH₂CHCH₂OCH₂CH=CH₂,
       |
       OH
(3-allyloxy-2-hydroxypropyl), and

—CH₂CHCH=CH₂, (2-hydroxy-3-butenyl).
       |
       OH

In step (a), cyanoacetic acid is reacted with lower dihydric alcohol to form a hydroxyalkyl cyanoacetate, as described in U.S. Pat. No. 3,644,466, Example 3, cols. 7–8.

In step (b), the hydroxy group of the hydroxyalkyl cyanoacetate then is protected by acylation, suitably with acetic anhydride, to give the corresponding acetoxyalkyl cyanoacetate.

Step (c) in the process involves a Knoevenagel condensation of a benzophenone with the acetoxyalkyl cyanoacetate. The Knoevenagel reaction is generally run in the presence of a solvent, such as benzene, toluene, or ethylenedichloride, under reflux, usually at a temperature between 80° and 100° C. for about 24 hours. The reaction preferably proceeds in a nitrogen atmosphere and in the presence of glacial acetic acid and ammonium acetate as a catalyst. Conventional washings of the product with water and saturated bicarbonate solution are done prior to the drying, removing the solvent, and recovering the product.

The fourth step (d) in the synthesis is to remove the protecting acetyl group by acid hydrolysis in alcohol to provide the corresponding free hydroxyalkyl compound. This step is carried out in methanol under acid conditions at reflux temperatures.

The final step (e) involves alkylation with a reactive ethylenic compound, such as an ethylenic halide e.g. allyl chloride or allyl bromide. The reaction is carried out in an inert solvent, suitably an aromatic or aliphatic hydrocarbon or ether hydrocarbon, such as, toluene, benzene, tetrahydrofuran, dioxane or ethylene dichloride, at a suitable temperature, generally ranging from room temperature to the reflux temperature of the solvent, e.g. if tetrahydrofuran, at about 66° C., and in the presence of a base, such as sodium hydride, the reactants are controlled to provide at least a 1:1 molar ratio of the ethylenic halide to the hydroxyalkyl 2-cyano-3,3-diphenyl acrylate. The reaction is run for about 1–6 hours at the reflux temperature.

The compounds of the invention may be copolymerized, for example, with a urethane oligomer, by radiation curing to provide useful polymeric coatings.

The following examples will describe the invention with more particularity.

EXAMPLE 1

2-(2-Cyano-3,3-Diphenylacryloxy)Ethyl Allyl Ether

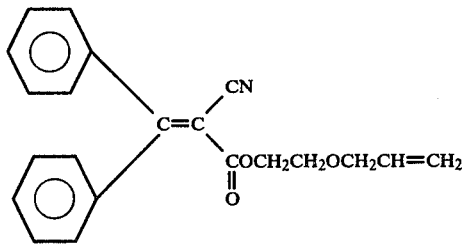

(a) 2-Hydroxyethyl 2-Cyanoacetate

Cyanoacetic acid was esterified with ethylene glycol according to U.S. Pat. No. 3,644,466 (col. 7–8, Ex. 3) to give the product in 74% yield.

(b) 2-Acetoxyethyl 2-Cyanoacetate

Into a three-neck round bottom flask with magnetic stirrer, dropping funnel, thermometer, and drying tube was charged 122 g. (1.2 moles) of acetic anhydride and 10 drops of concentrated sulfuric acid. Then 129 g. (1 mole) of 2-hydroxyethyl cyanoacetate was added dropwise with stirring while maintaining the reaction temperature below 75° C. The acylated ester thus produced was then diluted with 100 ml. of water and the excess acid was neutralized with solid potassium carbonate. The oil layer was separated and dried to yield 130 g. (79%) of the desired compound.

(c) 2-Acetoxyethyl 2-Cyano-3,3-Diphenylacrylate

A three-neck round bottom flask fitted with a mechanical stirrer, a thermometer and a Dean-Stark trap fitted with a reflux condenser was charged with 200 ml. of toluene, 182 g. (1 mole) of benzophenone, 205 g. (1.2 moles) of 2-acetoxyethyl 2-cyanoacetate, 40 ml. of glacial acetic acid, 16 g. of ammonium acetate. The contents were heated to reflux (110° C.) for 24 hours while the theoretical amount of water by-product was removed by azeotropic distillation. Upon removal of the solvent, as well as unreacted starting material by vacuum distillation, a yield of 200 g. (60%) of the desired product was obtained.

(d) 2-Hydroxyethyl 2-Cyano-3,3-Diphenylacrylate

A charge of 800 ml. of methanol, 335 g. (1 mole) of 2-acetoxyethyl 2-cyano-3,3-diphenylacrylate and 10 drops of concentrated hydrochloric acid was heated at 65° C. for 18 hours. Evaporation of the solvent left 235 g. (80%) of the intermediate compound as an amber, viscous oil.

(e) Into a round bottom flask equipped with magnetic stirrer, reflux condenser and drying tube was charged 20 ml. of dry tetrahydrofuran and 3.2 g. (0.011 moles) of 2-hydroxyethyl 2-cyano-3,3-diphenylacrylate and the solution is rapidly stirred. Then sodium hydride 0.79 g. (0.016 moles) as a 50% oil dispersion was added portionwise. To the resulting suspension was added 5.3 g. (0.044 moles) of allyl bromide and the mixture was heated at reflux (66° C.) for 5.5 hours. Upon cooling, a white insoluble solid (NaBr) was removed by filtration. The organic filtrate was evaporated, leaving as the desired product a pale yellow oil.

EXAMPLE 2

2-(2-Cyano-3,3-Diphenylacryloxy)Ethyl 2-Butenyl Ether

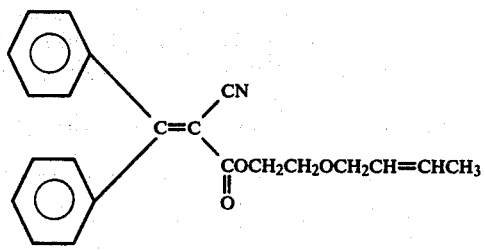

When crotyl bromide was substituted for allyl bromide in Example 1, the desired product is obtained.

EXAMPLE 3

2-(2-Cyano-3,3-Diphenylacryloxy)Ethyl 2-Methyl-2-Propenyl Ether

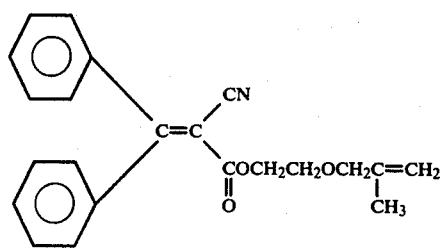

When 3-chloro-2-methyl-1-propene was substituted for allyl bromide in Example 1, the desired product is obtained.

EXAMPLE 4

2-(2-Cyano-3,3-Diphenylacryloxy)Ethyl Vinylbenzyl Ether

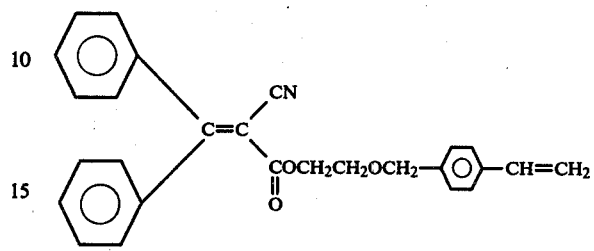

When vinylbenzyl chloride was substituted for allyl bromide in Example 1, the desired product is obtained.

EXAMPLE 5

2-(2-Cyano-3,3-Diphenylacryloxy)Ethyl Vinyloxyethyl Ether

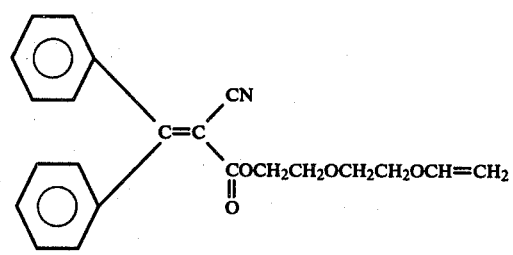

When chloroethylvinyl ether was substituted for allyl bromide in Example 1, the desired product is obtained.

EXAMPLE 6

2-(2-Cyano-3,3-Diphenylacryloxy)Ethyl 3-Allyloxy-2-Hydroxypropyl Ether

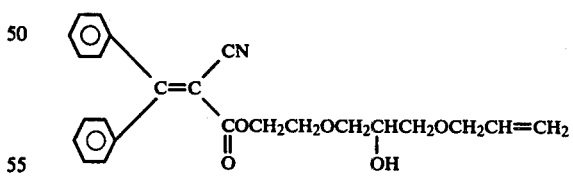

Into a round bottom flask was charged 29 g. (0.1 moles) of 2-hydroxyethyl 2-cyano-3,3-diphenylacrylate, 12.4 g. (0.11 moles) of allyl glycidyl ether and 250 mg. of tetramethylammonium chloride. The flask was stoppered and the mixture was heated at 50° C. for 16 hours. Then cooled mixture was diluted with 50 ml. methylene dichloride, treated with decolonizing charcoal and filtered. The filtrate was evaporated, leaving a pale yellow oil characterized as the product.

EXAMPLE 7

2-(2-Cyano-3,3-diphenylacryloxy)Ethyl 2-Hydroxy-3-Butenyl Ether

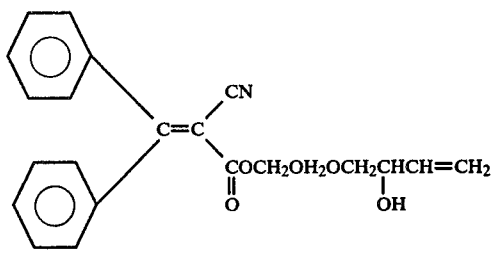

When butadiene monoxide substituted for allyl glycidyl ether in Example 6, the desired product was obtained.

EXAMPLE 8

Preparation of Radiation Cured Coating

Into a dry 1 l. resin kettle fitted with an air inlet tube, a stirrer, thermometer, and dropping funnel was charged 300.8 g. (1.3 moles) of isophorone diisocyanate and 4.8 ml. of a 10% (W/V) solution of dibutyltin dilaurate catalyst in ethylhexylacrylate. Dry air then was bubbled through the stirred solution while 322.1 g. (0.61 moles) of polyolcaprolactone (PCP-200) was added dropwise over 45 minutes. The solution then was heated to 80° C. and the reactants maintained at this temperature for 30 minutes. After cooling to 55° C., 160 mg. of phenothiazine was admixed. Then 151.9 g. (1.3 moles) of hydroxyethyl acrylate was added rapidly. The temperature was raised to 80° C. and maintained for 2 hours.

The resulting oligomer (58.1 g.) was formulated for coating by mixing with 25.4 g. of ethylhexylacrylate, 16.8 g. of vinyl pyrrolidone, 14.2 g. of hexanediol diacrylate, 1.8 g. of DC-193 silicone surfactant, 2.4 g. of Vicure-10 photoinitiator and 2.5 g. of 2-(2-cyano-3,3-diphenylacryloxy)ethyl allyl ether. The resulting syrup was coated onto a polyvinylchloride plate to form a film having a thickness of 1.5 mil. The film then was cured by ultraviolet radiation under an inert atmosphere to provide a tough, clear coatings containing the copolymerized UV absorber compound of the invention.

While certain preferred embodiments of the present invention have been illustrated by way of specific example it is to be understood that the present invention is in no way to be deemed as limited thereto but should be construed as broadly as all or any equivalents thereof.

What is claimed is:

1. Copolymerizable ultraviolet light absorber compounds having the formula:

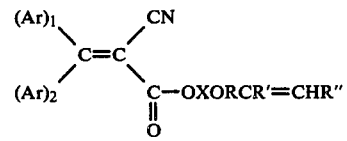

where $(Ar)_1$ and $(Ar)_2$ are phenyl;

X is alkylene, $C_2$–$C_{17}$, unsubstituted or substituted with halo, cyano, alkyl, alkoxy, alkoxyalkyl, or alkoxyalkyleneoxy, $C_1$–$C_6$; and, R is alkylene, oxyalkylene, alkyleneoxyalkylene, benzylene, $C_1$–$C_{10}$, unsubstituted or substituted with hydroxy; and R' and R" are independently hydrogen or alkyl, $C_1$–$C_6$.

2. Compounds according to claim 1 in which X is alkylene, $C_2$–$C_6$.

3. Compounds according to claim 1 in which —RCR'=CHR" is allyl, crotyl, methylpropenyl, vinylbenzyl, vinyloxyethyl, allyloxy-2-hydroxypropyl, or 2-hydroxy-3-butenyl.

4. Compounds according to claim 1 in which both $(Ar)_1$ and $(Ar)_2$ are phenyl, X is alkylene, $C_2$–$C_6$ and —RCR'=CHR" is allyl.

5. A compound according to claim 1 which is 2-(2-cyano-3,3-diphenylacryloxy)ethyl allyl ether.

6. A compound according to claim 1 which is 2-(2-cyano-3,3-diphenylacryloxy)ethyl 2-butenyl ether.

7. A compound according to claim 1 which is 2-(2-cyano-3,3-diphenylacryloxy)ethyl 2-methyl-2-propenyl ether.

8. A compound according to claim 1 which is 2-(2-cyano-3,3-diphenylacryloxy)ethyl vinylbenzyl ether.

9. A compound according to claim 1 which is 2-(2-cyano-3,3-diphenylacryloxy)ethyl 3-allyloxy-2-hydroxypropyl ether.

10. A compound according to claim 1 which is 2-(2-cyano-3,3-diphenylacryloxy)ethyl 2-hydroxy-3-butenyl ether.

* * * * *